(12) United States Patent
Calaresu et al.

(10) Patent No.: US 9,096,488 B2
(45) Date of Patent: Aug. 4, 2015

(54) PROCESS FOR THE ALKYLATION OF AROMATIC HYDROCARBONS WITH C1-C8 ALCOHOLS

(75) Inventors: Paolo Calaresu, Sassari (IT); Elena Bencini, Cerese di Virgilio (IT); Alessandro Casalini, Mantua (IT); Alessandro Del Seppia, Porto Matovand Mantua (IT); Giovanni Antonio Fois, Virgilio Mantua (IT)

(73) Assignee: VERSALIS S.P.A., San Donato Milanese (MI) (IT)

( * ) Notice: Subject to any disclaimer, the term of this patent is extended or adjusted under 35 U.S.C. 154(b) by 0 days.

(21) Appl. No.: 14/127,866

(22) PCT Filed: Jun. 21, 2012

(86) PCT No.: PCT/EP2012/061968
§ 371 (c)(1),
(2), (4) Date: Feb. 22, 2014

(87) PCT Pub. No.: WO2012/175614
PCT Pub. Date: Dec. 27, 2012

(65) Prior Publication Data
US 2014/0206909 A1   Jul. 24, 2014

(30) Foreign Application Priority Data
Jun. 23, 2011   (IT) .......................... MI2011A001143

(51) Int. Cl.
*C07C 37/08*   (2006.01)
*C07C 45/53*   (2006.01)
*C07C 2/86*   (2006.01)
*C07C 29/143*   (2006.01)

(52) U.S. Cl.
CPC ............... *C07C 2/864* (2013.01); *C07C 29/143* (2013.01); *C07C 37/08* (2013.01); *C07C 45/53* (2013.01); *C07C 2529/70* (2013.01)

(58) Field of Classification Search
CPC ............ C07C 45/53; C07C 37/08; C07C 2/86
USPC .................................. 568/798, 881; 585/467
See application file for complete search history.

(56) References Cited

U.S. PATENT DOCUMENTS 6,841,704 B2 *   1/2005   Sakuth et al. .................. 568/798

FOREIGN PATENT DOCUMENTS

EP    2298718 A1    3/2011
WO    0162692 A1    8/2001

* cited by examiner

*Primary Examiner* — Sikarl Witherspoon
(74) *Attorney, Agent, or Firm* — Tarolli, Sundheim, Covell & Tummino LLP

(57) ABSTRACT

Process for the alkylation of aromatic hydrocarbons by means of aliphatic alcohols containing from 1 to 8 carbon atoms, which comprises feeding the hydrocarbon and alcohol to the head of a fixed-bed reactor, operating with "trickle flow" regime, containing at least one layer of a catalyst comprising a zeolite selected from medium-pore zeolites and large-pore zeolites.

13 Claims, No Drawings

PROCESS FOR THE ALKYLATION OF AROMATIC HYDROCARBONS WITH C1-C8 ALCOHOLS

The present invention relates to a process for the alkylation of aromatic hydrocarbons with $C_1$-$C_8$ aliphatic alcohols.

More specifically, the present invention relates to a process for the alkylation of aromatic hydrocarbons containing from 6 to 10 carbon atoms with $C_1$-$C_8$ aliphatic alcohols.

In the case of an alcohol with two or more carbon atoms, mixtures composed of said alcohol and the corresponding olefin, i.e. the olefin with the same number of carbon atoms as the alcohol and which provides the same alkyl radical during alkylation, can also be used in the process of the present invention.

Even more specifically, the present invention relates to a process for the alkylation of benzene with isopropanol (IPA), or a mixture of isopropanol and propylene, to obtain cumene, and to the alkylation of benzene with ethanol, also ethanol from biomasses, possibly in a mixture with ethylene, to obtain ethylbenzene. The present invention also relates, in particular, to the alkylation of toluene with methanol to give xylenes, particularly para-xylene.

As is known, alkylated aromatic hydrocarbons are known chemical products that are used as intermediate products in numerous organic syntheses. Cumene, or isopropylbenzene, for example, is an important precursor for the production of phenol, in turn useful as intermediate for producing caprolactam from which nylon-6 is produced. Ethylbenzene is in turn the precursor of styrene, starting monomer for the synthesis of important thermoplastic materials such as polystyrene, ABS, SAN resins and other products.

Cumene and ethylbenzene, for example, are generally produced by the alkylation of benzene with propylene or ethylene in the presence of zeolitic catalysts such as X zeolite, Y zeolite or beta zeolite. These catalysts have substituted or are substituting traditional acid catalysts such as phosphoric acid or diatomaceous earth, for processes operating with fixed-bed reactors, or aluminium trichloride for processes operating with fluid-bed reactors. These traditional catalysts, in fact, have created problems of an environmental nature, for example relating to the disposal of the exhausted catalysts, and safety of the production plants subject to the risk of corrosion by acid materials.

The passage from traditional acid catalysts to zeolitic catalysts, however, has not allowed another problem to be overcome which is downstream of the synthesis of cumene. As already mentioned, cumene is the precursor for the production of phenol which is obtained by first oxidizing cumene to the corresponding hydroperoxide and then treating the latter with acid to obtain phenol. The acid treatment of cumene hydroperoxide, however, also produces, together with phenol, considerable quantities of acetone, generally 0.61 kg of acetone for each kg of phenol produced.

If, on the one hand, from an industrial point of view, for example, the simultaneous production of phenol and acetone in a single production unit can represent a positive aspect, on the other, due to the unbalanced commercial demand between the two products, the contemporaneous production of acetone represents, instead, a problem in managing an industrial plant for the production of phenol alone.

A first solution to the problem is described in U.S. Pat. No. 5,017,729 which describes a process for the production of phenol via cumene hydroperoxide characterized by the use of propylene coming from the dehydration of isopropyl alcohol, in turn obtained from the reduction of acetone in the presence of hydrogen.

European patent EP 1,069,099, on the other hand, describes an alkylation process of benzene with isopropanol, or mixtures of isopropanol and propylene, under pressure and temperature conditions corresponding to a complete gas phase of the mixture present in the reaction section and in the presence of a catalyst comprising a beta zeolite and an inorganic ligand. According to this patent, the cumene produced is oxidized to cumene hydroperoxide which, in turn, is treated with acids to give phenol and acetone. The acetone produced is then hydrogenated to isopropanol which is recycled to the alkylation unit.

European patent EP 1,069,100, on the other hand, describes an alkylation process, in the presence of zeolites, of aromatics with isopropanol, or mixtures of isopropanol and propylene, under liquid or mixed phase conditions, at pressures and temperatures which are such that the concentration of water in the liquid phase is not higher than 8,000 ppm with respect to the total quantity of water present. Also in this case, the cumene produced is oxidized to cumene hydroperoxide which, in turn, is treated with acids to give phenol and acetone. The acetone produced is then hydrogenated to isopropanol which is recycled to the alkylation unit.

International patent application WO10/143043 describes a process for the alkylation of benzene with isopropanol, or mixtures of isopropanol and propylene, which comprises effecting said alkylation reaction under gaseous or mixed phase conditions and in the presence of a catalytic system selected from zeolites belonging to the MTW family such as ZSM-12, CZH-5, Nu-13, Theta-3 and TPZ-12. The feeding of the reagents is effected from below. Also in this case, the cumene produced is oxidized to cumene hydroperoxide which, in turn, is treated with acids to give phenol and acetone. The acetone produced is then hydrogenated to isopropanol which is recycled to the alkylation unit.

Also for the synthesis of ethylbenzene, people have recourse to the use of ethanol, or mixtures of ethanol and ethylene, as described in international patent application WO 2010/029405 in which a catalyst containing MTW zeolite is used, and the reaction is carried out under gaseous or mixed phase conditions. The feeding of the reagents is effected from below. The ethanol used can derive from biomasses, in particular from the fermentation of sugars deriving from biomasses.

MI09A002289 describes the production of ethylbenzene by the reaction of benzene with ethanol, carried out at a pressure higher than atmospheric pressure, in the presence of a BEA-type zeolite, followed by a separation step.

Like the traditional alkylation processes of aromatic hydrocarbons which operate, for example, via ethylene or propylene, the processes of the known art mentioned above which use ethanol or isopropanol as alkylating agent, are also affected by the disadvantage of producing by-products such as, for example, polyalkylated aromatic hydrocarbons, which necessarily must then be converted into a monoalkylated product in specific units situated downstream of the alkylation section, for example, in one or more transalkylation units.

The objective of the present invention is therefore to provide an alkylation process of aromatic hydrocarbons with $C_1$-$C_8$ alcohols, for example methanol, ethanol, also produced from biomasses, or isopropanol (2-propanol), which allows a reduction in the formation of polyalkylated hydrocarbons and other by-products deriving from consecutive reactions, allowing the reaction yields to be significantly improved. The alcohols can be used in a mixture with the corresponding olefins. Undesired consecutive reactions which are substantially inhibited by operating according to the process of the present invention, are in particular, in addition to the polyalkylation reaction, isomerization reactions, such as, for example, the isomerization of para-xylene, deriving from the alkylation of toluene with methanol, to thermodynamically more stable isomers.

The object of the present invention, as is better described also in the enclosed claims, therefore relates to a process for the alkylation of aromatic hydrocarbons by means of aliphatic alcohols containing from 1 to 8 carbon atoms, which comprises feeding the hydrocarbon and alcohol to the head of a fixed-bed reactor, operating under "trickle flow" regime, containing at least one layer of catalyst comprising a zeolite selected from medium-pore zeolites and large-pore zeolites.

A preferred aspect of the present invention relates to a process in continuous for the alkylation of aromatic hydrocarbons by means of $C_1$-$C_8$ aliphatic alcohols in a fixed bed alkylation reactor which comprises:

a. mixing, in liquid phase, at least one aromatic hydrocarbon (A), the alcohol containing from 1 to 8 carbon atoms (B) and a recycled stream (C) coming from a discharge section of the alkylation reactor, b. feeding the final mixture obtained, pre-heated to the reaction temperature, to the head of a fixed-bed alkylation reactor, operating under "trickle flow" regime, containing at least one layer of catalyst comprising a zeolite selected from medium-pore zeolites or large-pore zeolites;

c. cooling the reaction mixture in a discharge section, to obtain an organic phase, comprising the alkylated aromatic hydrocarbon and an aqueous phase essentially consisting of reaction water;

d. subdividing the organic phase into a recycled stream (C), sent to the head of the alkylation reactor for the mixing phase with the reagents, and a final stream, comprising the alkylated aromatic hydrocarbon.

An even more preferred aspect of the present invention relates to a process in continuous for the alkylation of aromatic hydrocarbons by means of $C_1$-$C_8$ aliphatic alcohols in a fixed bed alkylation reactor which comprises:

a. mixing, in liquid phase, at least one aromatic hydrocarbon (A), and the $C_1$-$C_8$ alcohol (B) with molar ratios A/B higher than 1, preferably ranging from 1.5 to 5;

b. diluting the mixture coming from step (a) with a recycled stream coming from a discharge section of the alkylation reactor, so as to have a recycling weight ratio C/AB between the recycled stream (C) and the reagent mixture (AB) ranging from 1.5:1 to 10:1;

c. feeding the final mixture obtained, preheated to the reaction temperature, to the head of a fixed bed alkylation reactor, operating under "trickle flow" regime, containing at least one layer of catalyst comprising a zeolite selected from medium-pore zeolites or large-pore zeolites;

d. cooling the reaction mixture, directly downstream of the alkylation reactor, in a discharge section, to obtain an organic phase, comprising the alkylated aromatic hydrocarbon, and an aqueous phase essentially consisting of reaction water;

e. subdividing the organic phase into a recycled stream (C), sent to the head of the alkylation reactor for the mixing phase with the reagents, and a final stream, comprising the alkylated aromatic hydrocarbon.

The final stream thus obtained, as described further on, can then be sent to subsequent process steps.

According to an aspect of the present invention, in the case of an alcohol with two or more carbon atoms, mixtures of said alcohol and the corresponding olefin, i.e. the olefin with the same number of carbon atoms as the alcohol and which provides the same alkyl substituent by alkylation, can also be used in the process of the present invention.

When a mixture of alcohols and olefin is used, the molar ratio between said alcohol and the olefin preferably varies within the range of 10 to 0.1, more preferably from 5 to 1.

When a mixture of alcohols and olefin is used, the molar ratio between the aromatic hydrocarbon and mixture of the alcohol and corresponding olefin is greater than 1, preferably ranging from 1.5 to 5.

According to the present invention, the aromatic hydrocarbon preferably contains from 6 to 10 carbon atoms, even more preferably, it is selected from benzene, toluene and xylenes.

Any alcohol containing from 1 to 8 carbon atoms can be used in the present invention, even if it is preferably selected from methanol, ethanol, possibly mixed with ethylene, isopropanol, possibly in a mixture with propylene, t-butanol, possibly in a mixture with iso-butene, sec-butanol, possibly in a mixture with 2-butene, cyclohexanol, possibly in a mixture with cyclohexene, and mixtures thereof. Particularly preferred alcohols are methanol, ethanol, produced both by organic synthesis and fermentation of biomasses, and isopropanol.

In particular, when the aromatic hydrocarbon is benzene and the alcohol is ethanol or isopropanol, said reagents are fed, in liquid phase, to the alkylation reactor with weight ratios benzene/alcohol preferably ranging from 75/25 to 90/10, according to what has been previously specified in relation to the molar ratios between the process reagents.

In particular, the process of the present invention is conveniently used for the alkylation of benzene with ethanol, possibly mixed with ethylene, to give ethylbenzene and for the alkylation of benzene with isopropanol, possibly mixed with propylene, to give cumene. The process of the invention is also conveniently used for the alkylation of toluene with methanol to give xylene, in particular para-xylene: the undesired consecutive isomerization reaction of para-xylene to other isomers of xylene is inhibited under the conditions of "trickle flow" regime of the present invention.

The stream of aromatic hydrocarbon and the stream of $C_1$-$C_8$ aliphatic alcohol, possibly mixed with the corresponding olefin, can be premixed and then joined to the recycled stream (C), if said stream is used. Alternatively, the streams can be mixed together, each already at the reaction temperature or they can first be mixed together and then preheated to the operative temperature present inside the alkylation reactor.

If the recycled stream is used, the fresh reagents (AB) are mixed with said stream (C), with weight ratios C/AB preferably ranging from 2:1 to 6:1. The recycled stream, corresponding to part of the stream recovered from the alkylation reaction product after separation by demixing or decanting from the aqueous phase, is a stream mainly comprising the alkylated product and aromatic reagent in excess: a concentration of water equal to its solubility under the recycling temperature and pressure conditions can be present in the recycled stream.

The flow-rate of the reagents to the alkylation reactor is such as to provide a WHSV (Weight Hourly Space Velocity) which ranges from 1 to 8 hours$^{-1}$, for example and preferably from 2 to 6 hours$^{-1}$.

The process is carried out in continuous, and the reaction mixture, possibly also comprising the recycled stream, is fed to the head of the alkylation reactor operating with a "trickle flow" regime.

"Trickle flow" regime comprises operating in a three-phase, gas-liquid-solid situation wherein the catalyst is the solid phase, enveloped by the liquid and by the gas that pass through it in equicurrent from the top downwards, and it is a fluid-dynamic operative condition of a reactor for liquid/vapour reactions well-known to experts in the field, and described in detail in literature, for example in AIChE Journal, 1991, vol. 37 (2), page 202; Ind. Eng. Chem. Res., 1990, Vol. 29 (5), page 738; Ind. Eng. Chem. Res. 1997, 36, 3292-3314.

The flow regime type "trickle flow" is preferably obtained by managing the operative conditions of the alkylation reactor so as to have a gaseous phase essentially consisting of the reagents, and a liquid phase essentially consisting of the alkylation product, i.e. the monoalkylated aromatic hydrocarbon and possibly polyalkylated hydrocarbons. The water which is formed in turn by the reaction is distributed between the gaseous phase and the liquid phase, and is prevalently in gas phase.

Without adhering to any theory, it is held that under the conditions of the present invention, the liquid phase percolates through the catalytic bed and descends towards the bottom of the reactor causing only a partial wettability of the catalytic bed. This reduced contact with the catalytic bed could be the reason for which there is a lesser tendency of the alkylated hydrocarbon to produce polyalkylated hydrocarbons. The vapour phase, on the contrary, essentially consisting of the reagents, completely impregnates the catalytic bed, maximizing the contact with the catalytic active sites.

The reaction temperature inside the alkylation reactor preferably ranges from 160 to 250° C., more preferably from 180 to 230° C., with an internal pressure ranging from 1 to 10 MPa, more preferably from 1 to 5 MPa. An expert in the field is capable, for each aromatic substrate and for each alcohol, of selecting the temperature and pressure conditions that cause the presence of a gaseous phase and a liquid phase in the alkylation reactor operating under "trickle flow" regime, and in particular the pressure and temperature conditions that make it possible to operate with the reagents that are in gaseous phase and the products that are in liquid phase.

Any catalyst containing a medium- or large-pore zeolite can be used in the process, object of the present invention. In particular, MCM-22 is used as medium-pore zeolite. MCM-22 is described, for example in Science, 264, 1910-1913 (1994) and in U.S. Pat. No. 4,954,325.

Large-pore zeolite refers to a zeolite in which the pore openings consist of 12 tetrahedra. This corresponds in particular for zeolites based on silicon oxide and aluminium oxide, to pore openings consisting of twelve atoms, selected from silicon atoms and aluminium atoms, in tetrahedral coordination bound to each other by the sharing of an oxygen atom. Large-pore zeolites that can be conveniently used are zeolites of the type MTW, FAU, BEA, MAZ, MOR, OFF, SAPO-5, SAPO-11, preferably BEA, FAU and MTW.

The preferred catalyst is of the MTW type, particularly ZSM-12 zeolite. ZSM-12 zeolite is a porous crystalline material based on oxides which, in its anhydrous or calcined form, has a molar composition of the oxides corresponding to the following formula:

$$1.0\pm0.4M_{2/n}O\cdot W_2O_3\cdot 20\text{-}500YO_2\cdot zH_2O$$

wherein M is $H^+$ and/or a cation of an alkaline or alkaline-earth metal having a valence n, W is selected from aluminium, gallium or mixtures thereof, Y is selected from silicon and germanium, z varies from 0 to 60. M is preferably selected from hydrogen, sodium, potassium or mixtures thereof. W is preferably aluminium and Y is preferably silicon. W can be at least partially substituted by boron, iron or mixtures thereof. More detailed information on ZSM-12 zeolite is available in U.S. Pat. No. 3,832,449, in Ernst et al., *Zeolites*, September 1987, Vol. 7 and in Toktarev & Ione, Chon et al., *Progress in Zeolite and Microporous Material*, SSSC, Vol. 105, 1997.

According to an aspect of the present invention, the medium- or large-pore zeolite and, in particular, ZSM-12 zeolite, is preferably used in the form in which the cationic sites present in its structure are occupied for at least 50% by hydrogen ions. In particular, it is preferable for at least 90% of the cationic sites to be occupied by hydrogen ions.

The catalyst containing the zeolite, preferably ZSM-12 zeolite, is positioned in the reactor as a fixed bed that can consist of a single layer or a plurality of layers. The layers can be separated from each other so that a heat exchanger can be positioned in the intermediate space, that helps keep a constant vertical temperature profile inside the reactor.

The catalyst containing the medium- or large-pore zeolite, in particular, ZSM-12 zeolite, can be used as such or in bound form with an inorganic ligand. It can be in the form of extruded pellets or microspheres obtained by the technique known as spray-drying. These techniques are used with both the medium- or large-pore zeolite as such, or with the medium- or large-pore zeolite bound with an inorganic ligand. The inorganic ligand can be alumina, silica, silica-alumina, titanic, zirconia or clay. Alumina is the preferred ligand. If adopted, the inorganic ligand is used in such quantities as to give zeolite/ligand weight ratios ranging from 5/95 to 95/5, preferably from 20/80 to 80/20.

Using the process of the present invention, a drastic reduction in the formation of polyalkylated products is obtained, with respect to the corresponding processes which do not use reaction conditions with a "trickle-flow" regime, wherein said conditions with a "trickle-flow" regime, well-known to the expert in the field, comprise:
    positioning of the fixed bed catalyst,
    characteristic fluid-dynamic conditions and/or thermodynamic conditions inside the reactor associated with the fact that the feeding of the reagents is effected at the head of the reactor, with the fact that a gas phase coexist preferably and essentially consisting of the reagents and a liquid phase preferably and essentially consisting of the reaction products, wherein both phases pass through the catalytic bed in equicurrent,
    particular correlations between the linear rates of the liquid phase and gaseous phase.

Furthermore, recycling, when used, favours the disposal of heat, particularly inhibiting the formation of further by-products.

The reduction in polyalkylated products is important as it allows a reduction in the dimensions of the transalkylation section and distillation columns, downstream of the alkylation section, which represent a critical part of the overall alkylation process. This also leads to further advantages in terms of the consumption of transalkylation catalyst and utilities.

At the end of the alkylation step, the reaction mixture, comprising the alkylaromatic hydrocarbon, is discharged from the reactor and sent to a section where it is cooled to room temperature, for example from 20 to 40° C., and separated from the reaction water. The separation from the reaction water preferably takes place by demixing/decanting in specific equipment, where the organic phase is separated from the aqueous phase.

The organic stream that is collected after demixing can be divided into two sub-streams: one is used for the recycling, whereas the non-recycled part can have a purity which is such that it does not require subsequent treatment, or it can be sent to the remaining sections of the overall alkylation process which essentially comprise the transalkylation section, where the polyalkylated aromatic hydrocarbons are substantially transformed into monoalkylated product, and the purification section, where the monoalkylated aromatic product is recovered with a purity degree higher than 95% by weight.

If the monoalkylated aromatic product is cumene, this can be used, as is known, for producing phenol and acetone. The acetone produced together with the phenol can be recovered and transformed into isopropanol, as described for example in EP 379,323, and used as reagent in the alkylation process, object of the present invention.

A further object of the present invention therefore relates to a process for preparing phenol comprising the following steps:
(a) alkylation of benzene with isopropanol, and possibly propylene, to give cumene, in a fixed bed reactor containing at least one layer of catalyst containing a medium- or large-pore zeolite, which comprises feeding benzene and isopropanol, and possibly propylene, to the head of the alkylation reactor and operating in "trickle flow" regime, said alkylation being effected in accordance with one or more of the operative aspects specified above,
(b) oxidation of the cumene thus obtained,
(c) treatment of cumyl hydroperoxide with acids in order to obtain a mixture of phenol and acetone,
(d) hydrogenation of acetone to isopropanol which is recycled to step (a).

The present invention will now be explained in greater detail through the following examples for purely illustrative and non-limiting purposes.

EXAMPLE 1

135 g of a catalyst containing ZSM-12, prepared as described in Example 2 of US2003/0069459, are charged into a tubular, jacketed reactor heated by means of diathermic oil, having a diameter of 2.2 cm. 540 g/hour of a mixture of benzene/IPA, with a content of IPA (isopropanol) equal to 20% by weight with respect to the mixture, mixed with the effluent deriving from the same reaction, after elimination of the water by demixing/decanting, according to a recycling ratio of 4:1, are fed to the reactor from above. The reaction conditions are the following:
Temperature=190° C.,
Pressure=1.3 MPa These conditions correspond to operating in "trickle flow" regime, the reagents, benzene and isopropanol are fed from above, and are present in the reactor in gas phase, the alkylation products are present in the reactor in liquid phase. The attribution of the physical state of reagents and products is effected by comparison with the existing phase diagrams for the components in question, and also by calculation, adopting the RES state equation (Soave G. Chem. Eng. Sci. 27, 1197, (1972). The interaction parameters for this equation are obtained from the regression of the experimental data provided in literature relating to liquid-vapour equilibria and the mutual solubilities of the hydrocarbon-water mixtures (C. C. Li, J. J. McKetta Jul. Chem. Eng. Data 8 271-275 (1963) and C. Tsonopoulos, G. M. Wilson ALCHE Journal 29, 990-999, (19823)).

A quantitative conversion of IPA is obtained with a selectivity to cumene of 92%. The specific formation of diisopropylbenzenes is equal to 51.7 g per kg of cumene. The n-propylbenzene by-product is equal to 570 ppm with respect to the cumene formed.

EXAMPLE 2

135 g of the same catalyst containing ZSM-12 zeolite used in Example 1, are charged into a tubular, jacketed reactor heated by means of diathermic oil, having a diameter of 2.2 cm. 718 g/hour of a mixture of benzene/IPA, with a content of IPA equal to 15% by weight, mixed with the reaction effluent, after elimination of the water according to a recycling ratio of 4:1, are fed to the reactor from above. The hourly quantity of IPA fed to the reactor is the same as Example 1. The reaction conditions are the following:
Temperature=190° C.,
Pressure=1.3 MPa These conditions correspond to operating in "trickle flow" regime, the reagents, benzene and isopropanol are fed from above, and are present in the reactor in gas phase, the alkylation products are present in the reactor in liquid phase. The attribution of the physical state of reagents and products is effected as described in Example 1.

Under these conditions, a quantitative conversion of IPA is obtained with a selectivity to cumene of 94%. The specific formation of diisopropylbenzenes is equal to 35 g per kg of cumene. The n-propylbenzene by-product is equal to 570 ppm with respect to the cumene formed.

EXAMPLE 3

Comparative

An alkylation test of benzene with isopropyl alcohol is carried out using the experimental device described hereunder. The experimental device consists of tanks for the reagents benzene and isopropyl alcohol, feeding pumps of the reagents to the reactor, preheating unit of the reagents, steel reactor situated inside an electric heating oven, regulation loop of the temperature inside the reactor, regulation loop of the pressure inside the reactor, cooling system of the reactor effluent and collection system of the liquid and gaseous products. In particular, the reactor consists of a cylindrical steel tube with a mechanical sealing system and diameter equal to about 2 cm. A thermometer well having a diameter equal to 1 mm is positioned along the greater axis of the reactor, in which there is a thermocouple free to run along the greater axis of the reactor. A catalyst containing ZSM-12 zeolite, prepared as described in Example 2 of US 2003/0069459, is charged into the reactor. A quantity of inert material is charged above and below the catalytic bed for the completion of the same. The reagents benzene and isopropanol (IPA) are fed to the reactor, preheated and premixed in a specific mixer, with a flow from below. The reaction products are analyzed via gaschromatography. The reaction conditions at which the test is effected are as follows:
Reaction temperature: 190° C.
Reaction pressure: 0.8 MPa
WHSV: 4 hours$^{-1}$
[Benzene]/[IPA] in feed.: 3.25 moles/moles The fluid-dynamic regime obtained in this example does not correspond to operating under "trickle flow" regime. The reagents, fed with a flow from below, are in gaseous phase and the products partially in liquid phase, and the attribution of the physical state of the reagent mixture is effected as indicated in Example 1.

Under these conditions, a quantitative conversion of IPA is obtained, together with a selectivity to cumene of 82%. The specific formation of diisopropylbenzenes is equal to 147 g per kg of cumene. The n-propylbenzene by-product is equal to 1,000 ppm with respect to the cumene formed.

EXAMPLE 4

Comparative

Example 3 is repeated, operating at a pressure of 1.3 MPa. Under these conditions, the reagents prove to be in gaseous phase and the products in liquid phase. The fluid-dynamic regime obtained in this example does not correspond to operating under "trickle flow" regime. In this case, a 98% conversion of IPA is obtained, together with a selectivity to cumene of 87%. The specific formation of diisopropylbenzenes is equal to 91.2 g per kg of cumene. The n-propylbenzene by-product is equal to 800 ppm with respect to the cumene formed.

The invention claimed is:

1. A process for the alkylation of aromatic hydrocarbons by means of aliphatic alcohols containing from 1 to 8 carbon atoms comprising: feeding the hydrocarbon and alcohol to the head of a fixed-bed reactor, operating under "trickle flow" regime, containing at least one layer of catalyst comprising a zeolite selected from medium-pore zeolites and large-pore zeolites, wherein in the alkylation reactor, the aromatic hydrocarbon and aliphatic alcohol are in gas phase and the alkylation products are in liquid phase.

2. The process according to claim 1, carried out in continuous, which comprises:
   (a) mixing, in liquid phase, at least one aromatic hydrocarbon (A), a $C_1$-$C_8$ alcohol (B) and a recycled stream (C) coming from a discharge section of the alkylation reactor;
   (b) feeding the mixture obtained in step (a), pre-heated to the reaction temperature, to the head of a fixed-bed alkylation reactor, operating under "trickle flow" regime, containing at least one layer of catalyst comprising a zeolite selected from medium-pore zeolites and large-pore zeolites;
   (c) cooling the reaction mixture in a discharge section, to obtain an organic phase, comprising the alkylated aromatic hydrocarbon and an aqueous phase essentially consisting of reaction water; and
   (d) subdividing the organic phase into a recycled stream (C), sent to the head of the alkylation reactor for the mixing phase with the reagents, and a final stream, comprising the alkylated aromatic hydrocarbon.

3. The continuous process according to claim 1, which comprises:
   (a) mixing, in liquid phase, at least one aromatic hydrocarbon (A), and the $C_1$-$C_8$ alcohol (B) with molar ratios A/B higher than 1;
   (b) diluting the mixture coming from step (a) with a recycled stream coming from a discharge section of the alkylation reactor, so as to have a recycling weight ratio C/AB between the recycled stream (C) and the reacting mixture (AB) ranging from 1.5:1 to 10:1;
   (c) feeding the final mixture obtained, preheated to the reaction temperature, to the head of the fixed bed alkylation reactor, operating under "trickle flow" regime, containing at least one layer of catalyst comprising a zeolite selected from medium-pore zeolites and large-pore zeolites;
   (d) cooling the reaction mixture, directly downstream of the alkylation reactor, in a discharge section, to obtain an organic phase, comprising the alkylated aromatic hydrocarbon, and an aqueous phase essentially consisting of reaction water; and
   (e) subdividing the organic phase into a recycled stream (C), sent to the head of the alkylation reactor for the mixing phase with the reagents, and a final stream, comprising the alkylated aromatic hydrocarbon.

4. The process according to claim 3, wherein the recycling weight ratio C/AB between the recycled stream (C) and the reacting mixture (AB) ranges from 2:1 to 6:1.

5. The process according to claim 1, wherein the flow-rate of the reagents to the alkylation reactor is such as to provide a WHSV (Weight Hourly Space Velocity) ranging from 1 to 8 $hrs^{-1}$.

6. The process according to claim 1, wherein the reaction temperature inside the alkylation reactor ranges from 160 to 250° C. and the internal pressure ranges from 1 to 10 MPa.

7. The process according to claim 1, wherein the aromatic hydrocarbon is selected from benzene, toluene and xylene.

8. The process according to claim 1, wherein an alcohol containing from 2 to 8 carbon atoms is used in a mixture with an olefin having the same number of carbon atoms as the alcohol and which provides the same alkyl substituent by alkylation.

9. The process according to claim 1, wherein the alcohol is selected from methanol, ethanol and isopropanol.

10. The process according to claim 1, wherein the zeolite is a large-pore zeolite and is selected from MTW, FAU, BEA, MAZ, MOR, OFF, SAPO-5, and SAPO-11.

11. The process according to claim 10, wherein the large-pore zeolite is of the MTW type.

12. The process according to claim 1, wherein the zeolite is a medium-pore zeolite and is MCM-22 zeolite.

13. A process for the preparation of phenol, comprising the following steps:
   (a) alkylating benzene with isopropanol, and possibly propylene, to give cumene, effected in accordance with claim 1,
   (b) oxidating the cumene thus obtained,
   (c) treating cumyl-hydroperoxide with acids in order to obtain a mixture of phenol and acetone, and
   (d) hydrogenating the acetone to isopropanol which is recycled to step (a).

* * * * *